(12) United States Patent
Barba

(10) Patent No.: US 9,460,076 B1
(45) Date of Patent: Oct. 4, 2016

(54) METHOD FOR UNSUPERVISED LEARNING OF GRAMMATICAL PARSERS

(71) Applicant: Lexalytics, Inc., Amherst, MA (US)

(72) Inventor: Paul F. Barba, South Hadley, MA (US)

(*) Notice: Subject to any disclaimer, the term of this patent is extended or adjusted under 35 U.S.C. 154(b) by 0 days.

(21) Appl. No.: 14/941,724

(22) Filed: Nov. 16, 2015

Related U.S. Application Data

(60) Provisional application No. 62/081,253, filed on Nov. 18, 2014.

(51) Int. Cl.
*G06F 17/27* (2006.01)
*G06F 17/16* (2006.01)

(52) U.S. Cl.
CPC .......... *G06F 17/2715* (2013.01); *G06F 17/16* (2013.01); *G06F 17/274* (2013.01); *G06F 17/2775* (2013.01)

(58) Field of Classification Search
USPC ...................................................... 704/1–10
See application file for complete search history.

(56) References Cited

U.S. PATENT DOCUMENTS

| | | | | | |
|---|---|---|---|---|---|
| 4,868,750 | A | * | 9/1989 | Kucera | G06F 17/2775 704/8 |
| 5,752,052 | A | * | 5/1998 | Richardson | G10L 15/193 704/9 |
| 5,943,643 | A | * | 8/1999 | Van De Veen | G06F 17/271 704/2 |
| 2009/0192787 | A1 | * | 7/2009 | Roon | G06F 17/2715 704/9 |

* cited by examiner

*Primary Examiner* — Abul Azad
(74) *Attorney, Agent, or Firm* — Doherty, Wallace, Pillsbury & Murphy, P.C.

(57) ABSTRACT

The invention comprises a core algorithm to use language regularity in large collections of human created textual documents, as well as optimization techniques to make the algorithm tractable. The core algorithm includes receiving tuples of text units that may be grammatically linked and processing a stream of such tuples to discover language regularities. After this learning is completed, the algorithm's output is used to evaluate the perceived likelihood that different interpretations of novel sentences would have been intended by a speaker of the language.

18 Claims, 4 Drawing Sheets

METHOD FOR UNSUPERVISED LEARNING OF GRAMMATICAL PARSERS

BACKGROUND TO THE INVENTION

1. Field of the Invention

The present disclosure relates generally to textual analytics. More specifically, the disclosure relates to analysis of the syntactic structure of sentences.

2. Background of the Invention

Words in a sentence interact in varied ways. Verbs have subjects and objects which perform and are subject to the described action, respectively. Prepositional phrases modify only particular terms in a sentence. Identifying the relationships between each word to each other word is a powerful, but difficult task in allowing computers to reason about text. Current state of the art approaches focus on generating this language understanding by providing a computer with extensive human annotated sentences demonstrating human judgment on the proper parsing of a sentence. This process is expensive in human effort and has significant challenges in adapting to new and/or different domains of discourse or language, where all new annotations are needed.

SUMMARY OF THE INVENTION

Instead of providing a small amount of human prepared text, the invention instead makes use of large quantities of easily obtained unannotated text, such as newswire stories, social media posts, or Wikipedia articles. Each sentence from these sources does not contain any specific evidence about how the sentence should be interpreted. However, across a very large source of data, certain regular patterns of language use emerge. Matrix or tensor Factorization techniques are applied to data extracted from the provided text corpus to learn these data regularities, which are then used to evaluate the likelihood of all possible parses of a sentence. By varying the input corpus, specialized domains, such as, e.g., legal text, can be analyzed within domain knowledge without requiring humans to perform additional annotation. Further, phrase parsing techniques and hand generated or machine learned rules are preferably used to reduce the state space of the problem to one tractable on modern computers in sub-second timeframes.

DETAILED DESCRIPTION OF THE INVENTION

Definitions

Figure 1:
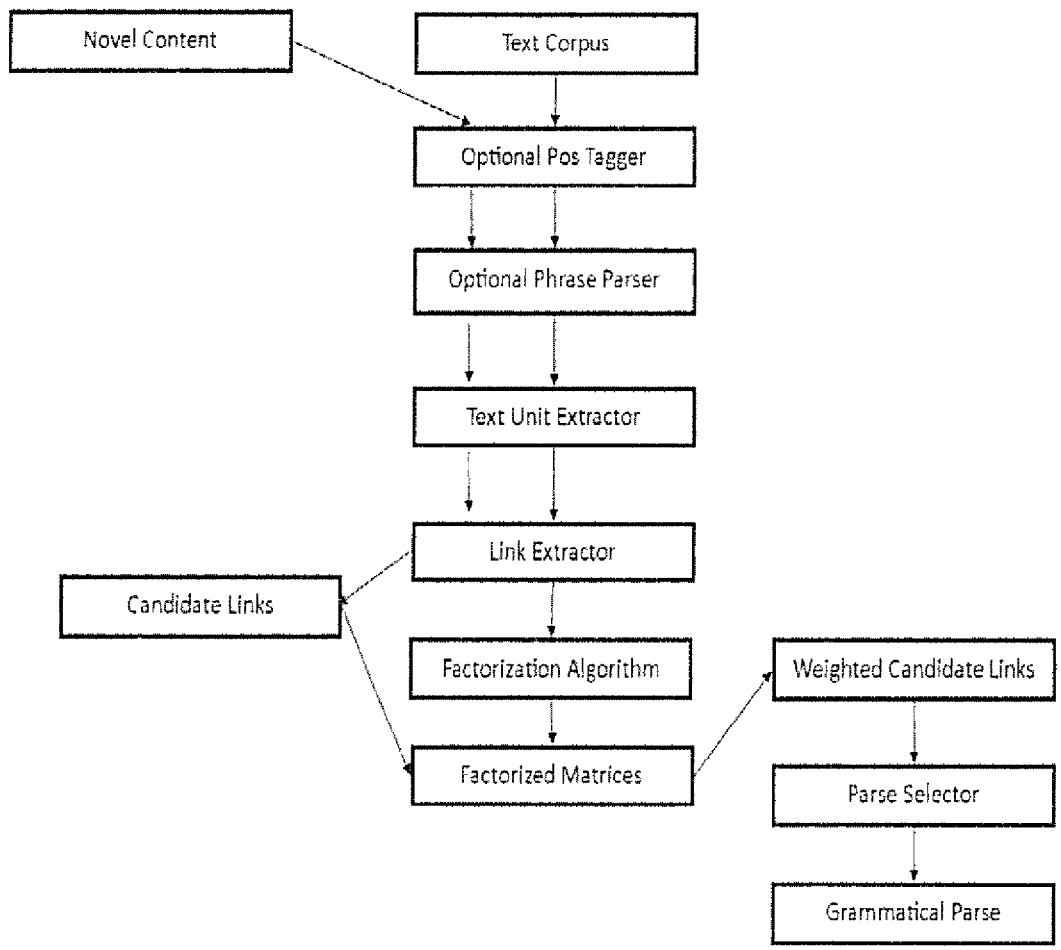
FIG. 1 is a schematic depicting an exemplary method.

Grammatical Parser—An algorithm that, when given text (often tokenized and part of speech tagged), produces a network (usually a tree) describing the interactions between words in the provided text.

Unsupervised Learning—A subclass of machine learning algorithms that detect regularities in a sample dataset without human involvement, in contrast to supervised learning where the dataset has been presorted into examples of the classes that the user wishes the machine to sort novel data into.

Matrix Factorization Algorithm—Any of a number of algorithms that approximate a provided or sampled matrix as the product of two or more calculated matrices.

Tensor Factorization Algorithm—Any of a number of algorithms that approximate a provided or sampled tensor as the product of two or more calculated matrices or tensors.

Online Factorization Algorithm—A factorization algorithm that updates the calculated matrices or tensors as it obtains samples from the matrix of interest, generally avoiding explicitly representing the original matrix or tensor being factorized. This is in contrast to algorithms that obtain all the samples or the entire matrix or tensor and then directly compute the factorized matrices or tensors.

Autoencoder—A neural network or deep learning algorithm designed to recreate its input signals, often used to learn features for more efficiently encoding signals.

Latent semantic analysis (LSA) algorithm—An algorithm which uses singular value decomposition (SVD) factorization to compute a semantic vector representation of words in a corpus based on their co-occurrences. This is a common, but not exclusive, concept representation algorithm that turns a collection of documents into a representation of words and documents in terms of learned concepts.

Clustering Algorithm—An algorithm which, given a large set of samples in some real or abstract space, groups the samples into clusters in a way that promotes intragroup similarity and intergroup dissimilarity.

Cross Product—The vector perpendicular to two other vectors.

Minimum Spanning Tree—Given a weighted network (that is, a series of nodes connected by edges where the edges are each assigned a weight) the minimum spanning tree is the set of edges that will connect all nodes into a single tree with the smallest total weight.

The invention comprises a core algorithm to use language regularity in large collections of human created textual documents. The invention further comprises optimization techniques to make that algorithm tractable. The core algorithm receives tuples of text units that may be grammatically linked, and processes a stream of such tuples to discover language regularities. After this learning is completed, the core algorithm's output is used to evaluate the perceived likelihood that different interpretations of novel sentences would have been intended by a speaker of the language.

First, the core algorithm will be described. A description of the optimizations will then follow.

The core algorithm operates on a substantial stream of sentences taken from human writing, such as, e.g., the full contents of Wikipedia. Each sentence is processed one at a time, or in parallel across multiple threads, processors or machines in one or more computers. A sentence may be split into smaller units referred to herein as "text units," wherein, in the simplest case, a single text unit is an individual word. These text units are then joined into possible grammatical links, wherein, in the simplest case, a grammatical link is a set of all combinations of words of some fixed size, generally two or three words, to form all word pairs or triples.

These grammatical links are then encoded. In the simplest case, e.g. the grammatical links may be encoded as just, e.g., the text of the words, and in a fuller implementation, e.g., the grammatical links may be encoded as, e.g., features. The features may be learned by an unsupervised learning technique, such as, e.g., an autoencoder. Alternatively, the features may, e.g., be human engineered. The features may include, e.g., one or more of a part of speech tag of each term generated by a part of speech tagging algorithm (a "POS-Tagger"), a distance between the terms, a learned representation of the sentence as a whole—as might be the output of a LSA algorithm, cluster membership generated from a clustering algorithm run previously on the content stream, and the like. An online factorization algorithm may be used to learn two or more matrices that are multiplied together to approximate, e.g., the frequency pairs or triples of representations of text units appearing as possible grammatical links in the representative corpus.

Because the input is an unmodified stream of text, any corpus or combinations of corpora can be used to generate the factorized matrices and power the grammatical parse. This allows quick adaptation to new domains or languages. For example, biology research papers and informal movie reviews use different terminology and common sentence structures, so each can be handled by its own dedicated parser trained on representative text.

To create a grammatical parse on a novel piece of text, the beginning of the core algorithm may be repeated. For example, the text may be broken into sentences, and then further split into text units. Text units are then joined into possible grammatical links. Each text unit in a tuple may be identified as a row, column or matrix in a particular factorized matrix or tensor. The cross product of the relevant vector, which may be multiplied by any other matrix that was output by the online factorization algorithm, is calculated to derive a value or score roughly equating to a measure of the probability that such a tuple of text units would be grammatically linked. These scores may then be used to select a most likely full grammatical parse of the sentence.

In one likely instantiation, use of the scores to select a full grammatical parse of a sentence includes finding the minimum spanning tree of the text units joined into grammatical links. In a simpler instantiation, a cutoff may be used, and all scores above the cutoff may be included. In a third instantiation the scores may be used as inputs to a human designed algorithm that encodes known grammatical knowledge, such as that a conjunction only joins a single pair of words (treating commas in lists as a conjunction here) or that a verb is linked to at most two noun phrases.

The basis on which the core algorithm works is that the decision on how to parse an ambiguous statement is often based on shared expectations of speakers. For example, in the sentence "my dog and I barked and cheered at the passing parade," the subject of the two verbs present (barked, cheered) is ambiguous. The dog and the speaker could both be the subject to either verb or both. However, the expectation is that a dog will bark and a speaker might cheer, but that neither will do the other. Across many sample pieces of text three will be many cases of dogs barking, and few cases of dogs cheering, and so the factorized representation of the term co-occurrences in the representative corpus will cause this novel sentence to be parsed as the dog barking and the speaker cheering, both at the parade.

In a more complicated scenario, consider the verb "tossed." A number of objects are frequently tossed, such as baseballs, pencils, and keys. It is not expected, however, to see a sentence where the word "tossed" appeared with an object such as, e.g., the word "mountain", "sadness" or "Jupiter." Factorization algorithms can compress a large set of observations by detecting regularities in language. For example, the algorithm is expected to discover that baseballs, pencils and keys are all similar objects in that they can all be "tossed."

From this, the algorithm can simultaneously discover a class of verbs that operate on small, holdable objects, such as the verbs "dropped", "held" and "juggled." These regularities may be encoded into the factorized matrices and may allow novel situations to be sensibly analyzed. For example, "juggled my keys" and "juggled the stairs" might be possible interpretations inside a sentence, with neither phrase having appeared anywhere in the training corpus. However, "juggled" will have been somewhat connected to the class of verbs performed on small objects, and "keys" will have become at least a partial member of that class, while "stairs" is likely to have been learned as explicitly not in that class. In this manner, the approach can generate probable parses of sentences containing novel usages of words in the training corpus.

Matrix factorization is a wide field with many algorithms. The general idea, however, is to represent a large series of observations, in this case the pairing of all text units, as the product of two or more smaller matrices. These smaller matrices are often more tractable to store and operate on. Additionally, the compression to smaller matrices requires the algorithm to find general patterns in the data, thereby allowing similar cases to influence each other, and novel pairings of text units to have sensible interpretations.

In the case where two matrices are used, the rows of the first matrix may encode one or more aspects of one of the text units that would make that text unit(s) more or less likely to appear together in a grammatical link with the second text unit. In cases where three or more matrices are used, the additional matrices provide a layer of indirection between the representations of the two text units, allowing, e.g., different features to be selected as salient for the desired relationship. In higher dimensional cases, additional indirection can be leaned, thereby allowing, e.g., a particular row to encode different information in different cases.

Tensor factorization performs the same operations on a three or more dimensional extension of a matrix. For example, the triple "boy, patted, dog" requires 3 dimensions to represent it. By using a tensor, the word "patted" can be learned as a matrix that encodes separate probabilities for each possible subject to act on each possible object. In the matrix case, this could be represented as two unlinked pairs: "boy patted" and "patted dog."

An alternative use of a tensor, e.g., is to encode pairs such as "patted dog" along with a representation of the context in which the pair appeared, such as a classification of the topic of the document where the pair occurred. Tensor factorization is generally a slower process than matrix factorization, but otherwise proceeds very similar to the matrix factorization.

Many matrix and tensor factorization algorithms exist to perform generalization of one matrix or tensor into multiple smaller matrices or tensors, with the various algorithms having different performance profiles and presumptions about the data being factorized. One skilled in the art is capable of choosing an appropriate and standard factorization algorithm for the performance desired.

Besides appropriate choice of the factorization algorithm, other optimizations are important for a reasonable performance window. A naïve implementation, e.g., would compare all word pairs, requiring $O(mn^2)$ operations, where n is the number of words in a sentence and m is the number of features used in the factorized matrices. Additionally, while approximately $O(n)$ grammatical links exist in a sentence, $O(n^2)$ are selected in an unsupervised manner during training, resulting in a low signal to noise ratio and thus a high training corpus size and runtime requirements.

In an exemplary method, a phrase parser is preferably used as a first pass to the full grammatical parse. The phrase parser preferably identifies tightly linked grammatically phrase structures, such as noun phrases and verb phrases. For example, in the sentence "The red bike is on the sidewalk," an analysis of the English language will show that the initial "the" cannot modify any term but "bike" in this sentence, and that the latter "the" cannot modify any term but "sidewalk" in this sentence. Additionally, an adjective located between an article and a noun must modify that noun, so "the red bike" is certain to be a single noun phrase. In such a manner, this sentence can be grouped into three phrases: "the red bike", "is" "on the sidewalk". Such phrases can be encoded by speakers of a language manually in reference to the parts of speech and semantic classes of the terms.

Alternatively, from a corpus of sentences parsed by humans, trained machine learning algorithms can discover such regularities. Alternatively, from a corpus unparsed by humans and with a clustering or other unsupervised algorithm and a part of speech tagger for the language, these regularities can be discovered. The phrases formed with a phrase parser can be used as the text units, reducing the number of text units in a sentence, thereby reducing runtime and incorrect parses seen during training.

When a phrase is used as a text unit, the phrases can be used in their entirety as the rows and columns of the matrix or tensor, although this can lead to data sparsity issues. In one solution, just the first and last word may be used such that "the red bike" from earlier becomes "the bike" and "on the sidewalk" becomes "on sidewalk." Alternatively, the phrases can be represented as a set of features as previously discussed herein.

For fuller performance optimization, a set of possible phrase links can be developed. Such phrase links may restrict the domain from the pairwise combination of all phrases to only links viewed as reasonable by a human speaker, or learned as earlier from an annotated corpus set via machine learning. For example, "[Noun] [conjunction] [verb]" is not a well formed English clause. That is, it is difficult to imagine a sentence incorporating "the blue bird and was swimming." Rejecting such a possible subparse at the very start further reduces the state space of this algorithm.

The invention shall further be described with reference to the drawings, wherein it is to be understood that the drawings are representative of the invention, and that all embodiments not expressly depicted in the drawings and as would occur to one of ordinary skill in the art are contemplated and included herewith.

FIG. 1 demonstrates exemplary components of the invention and their interactions. A large text corpus from the language and domain desired to be parsed is collected and provided to the algorithm. This text is optionally POS-tagged and grouped into phrases based on the distribution of POS-tags. Text units may then be extracted from the corpus, usually words or phrases, optionally with additional features provided from an external algorithm. Possible links may then be enumerated, often all pairs or triples within a sentence, or according to human coded or learned restriction patterns, e.g. These links may be provided online or in batch, e.g., to a matrix or tensor factorization algorithm which respectively provides factorized matrices or factorized tensors.

For evaluation of a novel sentence, the optional POS-tagging and phrase groupings are applied, followed by extraction of text units, and then enumeration of possible links. Two or more vectors or matrices may be obtained from the factorized matrices or tensors from the previous section, which may be multiplied together to get a likelihood score. The collection of text unit links and their corresponding scores are provided to a parse selector, such as, e.g., a simple weight cutoff, minimum spanning tree algorithm, and the like. The parse selector may provide one or more subsets of the text unit links, which are taken to be the parse diagram for the novel content.

Figure 2:
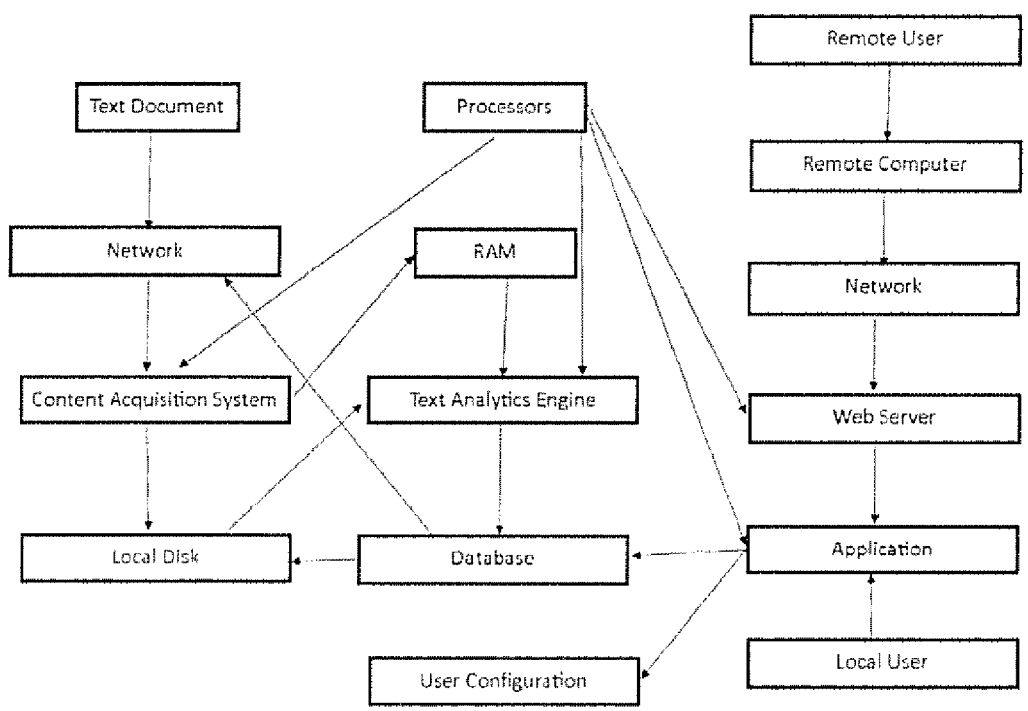
FIG. 2 is a schematic further depicting the method depicted in FIG. 1.

FIG. 2 demonstrates the larger context in which the disclosed method may operate. Text documents may be provided via a local or global network to a machine, including e.g., at a minimum, processors and RAM, via a content acquisition system. The text analytics engine, including the grammatical parser, may be run on one or more processors on the text obtained via the content acquisition system and stored in RAM or on disk. The text analytic engine optionally obtains configurations from RAM or disk, and produces metadata about the document provided via the content acquisition system. This metadata may include facts about the document such as, e.g., sentiment, named entities, grammatical parses, word counts, as well as many other outputs designed to describe, summarize and synthesize the document. Documents may be optionally batched together into collections and analyzed simultaneously. In one exemplary embodiment, the metadata is stored in a database, although the results may also be displayed directly to a user, provided directly to additional computer algorithms, written directly to disk, stored temporarily in RAM, and the like.

A remote or local user can access one or more applications (e.g., across a network and webserver in the case of, e.g., a remote user), optionally to control the configuration of the content acquisition and text analytics engine, to view and interact with the metadata created by the text analytics engine or the synthesis of that metadata, to interact with other applications which themselves make use of the metadata, and the like.

Figure 3:
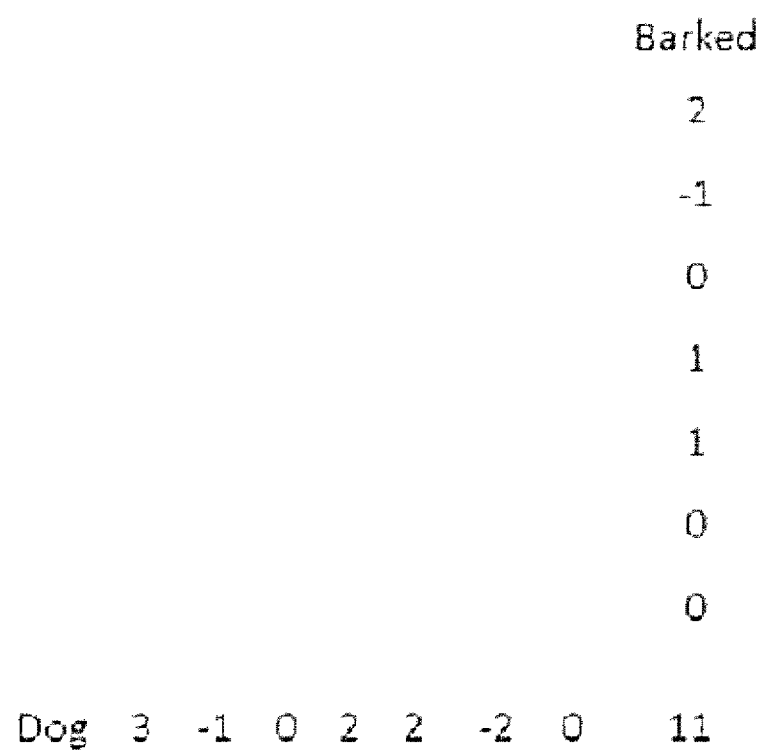
FIG. 3 is a schematic depicting a sample subset of the weighting of a possible text unit link.

FIG. 3 demonstrates a sample subset of the weighting of a possible text unit link, in this case the word pair "dog" and "barked." In general, the vectors are larger, but for ease of understanding vectors of size, 7 vectors are used by way of example. Each vector exists in the factorized matrices, either locally or hashed across memory depending on implementation. The corresponding row and column are pulled out. For simplicity, two vectors multiplied directly are shown in FIG. 3, but additional matrices, tensors, and vectors can be included to encode additional information. In the case shown in FIG. 3, the dot product, or the sum of the products of corresponding rows and columns are calculated. In this ease the corresponding rows and columns, multiplied together and then added up, produce a score of 11, which would be expected to be substantially higher than a word pairing such as "dog" and "meow."

Figure 4:
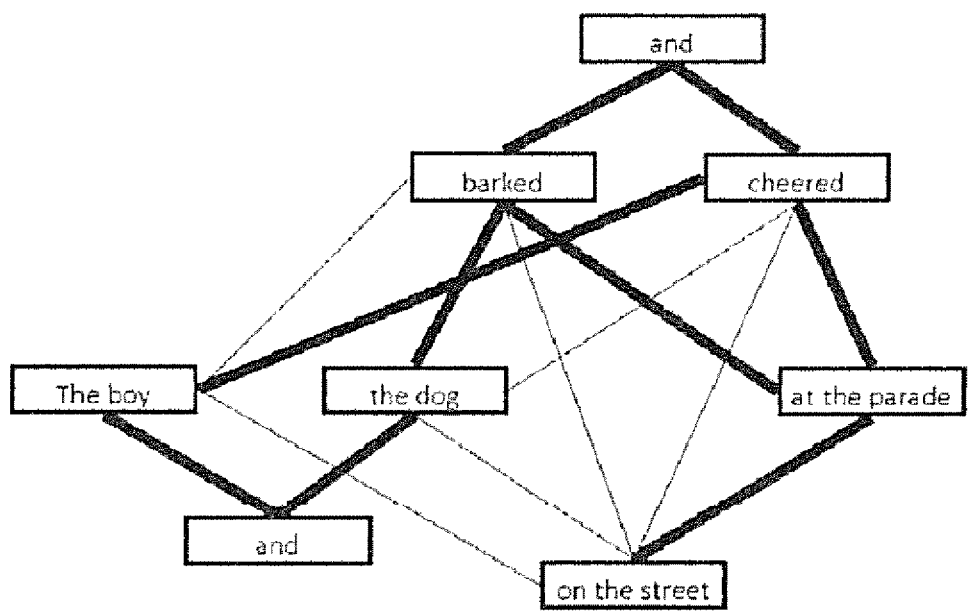
FIG. 4 is a schematic depicting possible links and final parse decisions by an embodiment of the disclosed method on a representative sentence.

FIG. 4 demonstrates the possible links and final parse decisions by an exemplary embodiment of the disclosed method on the following sentence: "The boy and the dog barked and cheered at the parade on the street." In this example, the sentence is broken down into the following, nodes or phrases: "the boy", "and", "the dog", "barked", "and", "cheered", "at the parade", and "on the street." In a different embodiment, each word may have been treated as an individual node, or different phrase boundaries may have been selected.

In an exemplary embodiment, all of the nodes would have an edge between them. Additionally, in the demonstration shown in FIG. 4, certain grammatical regularities are exploited to reduce the state space. For example, conjunctions do not join noun phrases and verb phrases in English, and conjunctions do not usually cross verb phrases to join two noun phrases.

Each edge is provided a weight. An algorithm may be used to select from the weights, wherein such an algorithm may include, e.g., a minimum spanning tree algorithm, or the provision of a cutoff. The bold lines depicted in FIG. 4 correspond to the edges selected by the parse selection algorithm. These edges are used to provide additional information to, e.g., a user of a text analytics application, or to other text analytics algorithms run on this enhanced version of the original text.

What is claimed is:

1. A method for unsupervised learning of a grammatical parser and the use thereof, wherein the method comprises:
   providing a processor on a computer, wherein the processor runs a content acquisition system to obtain a corpus of text documents over a computer network;
   storing the corpus of text documents from the content acquisition system on a storage device;
   providing a processor on the computer which runs a text analytics engine, wherein the text analytics engine comprise a core algorithm, and a factorization algorithm;
   using the core algorithm to:
      divide the corpus of text documents into a plurality of sentences;
      divide the sentences from the plurality of sentences into a plurality of text units;
      join the text units from the plurality of text units into a plurality of grammatical links; and
   using the factorization algorithm to factorize a matrix or a tensor for each of the grammatical links of the plurality of grammatical links to respectively generate a plurality of factorized matrices or a plurality of factorized tensors; and
   additionally using the core algorithm to:
      generate parses from a corpus of a novel document, comprising:
         divide the corpus from the novel document into a plurality of sentences;
         divide the sentences from the plurality of sentences from the novel document into a plurality of text units;
         identify a subset of all possible grammatical links from the plurality of text units from the novel document; and
         determine the relative likelihood of the grammatical links in the corpus of the novel document by using the factorized matrices or the factorized tensors to compute a score representing the likelihood of the grammatical links.

2. The method of claim 1, wherein the text units from the plurality of text units from the corpus of text documents are individual words in the sentences from the plurality of sentences of the corpus of text documents.

3. The method of claim 1, further comprising speech tagging the text units from the plurality of text units from the corpus of text documents into phrases.

4. The method of claim 3, further comprising storing the phrases in a respective factorized matrix or a factorized tensor as a first and a last word of the phrase.

5. The method of claim 1, further comprising classifying the text units from the plurality of text units from the corpus of the novel document against a human generated set of rules to narrow down the number of possible grammatical links.

6. The method of claim 1, further comprising updating the factorized matrix as new content is processed, wherein updating the factorized matrix includes use of an online factorization algorithm.

7. The method of claim 1, comprising both factorization of a matrix and a tensor, wherein factorizing the tensor includes encoding verbs from the text units of the plurality of text units from the corpus of text documents into a tensor with subjects and objects, and wherein factorizing the matrix includes encoding non-verbs from the text units of the plurality of text units from the corpus of text documents.

8. The method of claim 1, further comprising using a minimum spanning tree to combine the scored text unit links into a single parse.

9. The method of claim 1, further comprising providing a cutoff, wherein scores above the cutoff are used to determine the relative likelihood of a grammatical link.

10. The method of claim 1, further comprising generating features of the text units from the plurality of text units from the corpus of the novel document, and placing those features as additional rows and columns in the factorized matrix or the factorized tensor.

11. The method of claim 10, wherein the features of the text units are generated by an autoencoder.

12. The method of claim 10, wherein the features are an output of a semantic representation algorithm.

13. The method of claim 1, wherein the tensor to be factorized is a triple of the linked text units from the plurality of text units from the corpus of the documents being matched and a representation of the context in which the linked text units appear.

14. The method of claim 13, further comprising generating a plurality of semantic word vectors from the plurality of sentences from the corpus document, and wherein the representation of the context is a sum of the plurality of semantic word vectors.

15. The method of claim 14, wherein generating the plurality of semantic word vectors includes using a latent semantic analysis algorithm.

16. The method of claim 1, further comprising sorting the corpus of text documents into individual document classes, and generating a factorized matrix or a factorized tensor from each of the individual document classes, sorting the corpus of the novel document into individual document classes, and using the factorized matrix or the factorized tensor generated from each of the individual document classes to parse the novel document.

17. The method of claim 1, wherein the identification of grammatical links in the corpus of the novel document is restricted to follow grammatically sound rules provided by a human.

18. The method of claim 1, wherein the identification of grammatical links in the corpus of the novel document is restricted to follow a set of grammatically sound rules learned via a classifier on an annotated sample of document parses.

* * * * *